United States Patent [19]

Belyaev et al.

[11] 4,119,495

[45] Oct. 10, 1978

[54] METHOD FOR PROCESSING ACTIVATED SLUDGE INTO USEFUL PRODUCTS

[76] Inventors: Vasily Dmitrievich Belyaev, pereulok Sivtsev Vrazhek, 33, kv. 5; Sergei Vladimirovich Chepigo, Leningradsky prospekt, 74, korpus 2-a, kv. 9, both of Moscow; Nina Ivanovna Korotchenko, ulitsa Furmanova, 14, Tomilino Moskovskoi oblasti; Alexandr Nikolaevich Mezentsev, K-482, korpus 345, kv. 37, Moscow; Olga Vasilievna Samokhina, Dmitrovskoe shosse, 29, kv. 187, Moscow; Alexandra Leonidovna Krasinskaya, Leningradsky prospekt, 78, kv. 278, Moscow; Vadim Nikolaevich Timkin, K-482, korpus 338-b, kv. 60, Moscow; Yaroslav Yaroslavovich Shkop, Tverskoi bulvar, 26, kv. 26, Moscow; Alexei Olegovich Colubev, Kolokolnikov pereulok, 17/20, kv. 16, Moscow, all of U.S.S.R.

[21] Appl. No.: 761,253

[22] Filed: Jan. 21, 1977

[51] Int. Cl.$^2$ ............................ C02C 1/02; A23J 1/00; A23K 1/00; C12B 3/00
[52] U.S. Cl. ................................ 195/102; 260/112 R; 210/18; 426/635; 426/656; 195/28 R
[58] Field of Search ................... 195/27, 28, 82, 100, 195/102, 104; 260/112 R; 210/18

[56] References Cited

U.S. PATENT DOCUMENTS

| 2,544,273 | 3/1951 | Miner, Jr. et al. | 195/37 |
| 3,585,179 | 6/1971 | Samejima et al. | 260/112 R |
| 3,718,541 | 2/1973 | Kalina | 195/28 R |
| 3,862,112 | 1/1975 | Ishida et al. | 195/28 R |
| 3,936,375 | 2/1976 | Nettli | 260/112 R X |

*Primary Examiner*—Lionel M. Shapiro
*Attorney, Agent, or Firm*—Steinberg & Blake

[57] ABSTRACT

A method for processing activated sludge into useful products comprises hydrolysis of activated sludge at a pH of 0.01 to 6.0 at a temperature of 50° to 150° C with subsequent separation of formed water-soluble protein, carbohydrate and mineral substances and vitamins, and/or alkaline extraction of the initial activated sludge at a pH of 9 to 13 at a temperature of 40° to 90° C with subsequent separation of proteins from the extract.

The invention makes it possible to simultaneously obtain useful products and solve the problem of utilization of activated sludge formed in great excess in biological purification of effluents, thereby ensuring intensification of purification of effluents, improvement of the quality of the purified water and decrease in the pollution of the environment.

8 Claims, 1 Drawing Figure

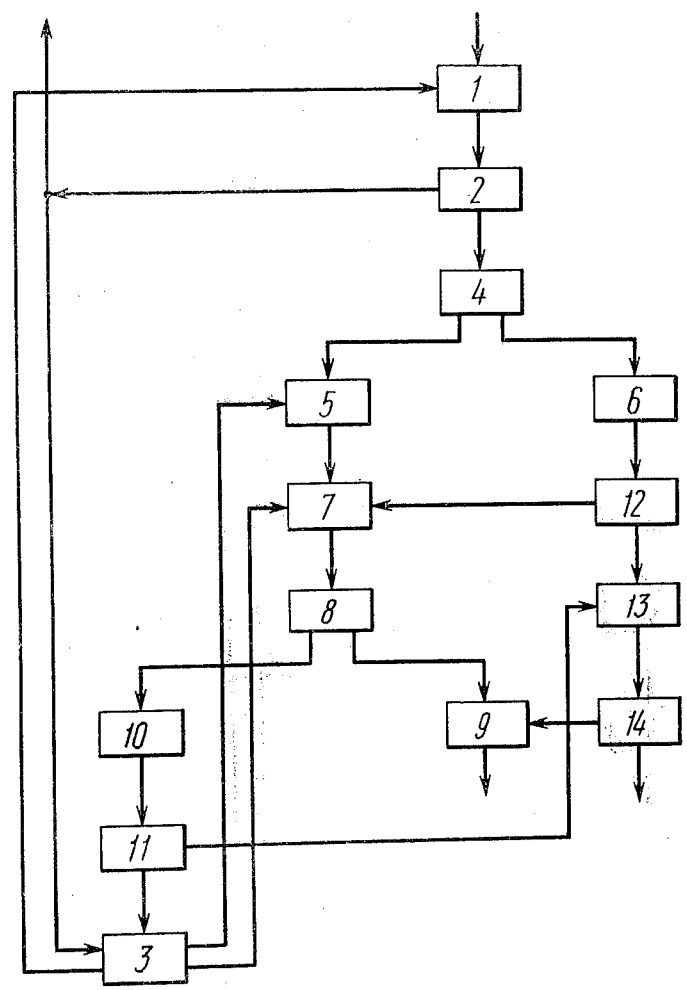

METHOD FOR PROCESSING ACTIVATED SLUDGE INTO USEFUL PRODUCTS

The present invention relates to the field of biological purification of effluents, and more particularly, to a method for processing excess activated sludge and the manufacture of useful products thereby.

The problem of environment conservation demands organization of effective purification of effluents. In the biological purification of effluents considerable amounts of excess activated sludge are formed which is a waste product. This excess activated sludge which is a product of microbiological synthesis contains such valuable substances as proteins, carbohydrates, lipids, vitamins, nucleic acids and mineral substances, like any other biomass of microorganisms.

Utilization of excess activated sludge represents a serious and difficult problem due to the fact that a suspension of activated sludge contains a vast amount of water (98 to 99.5%) and is distinguished by instability of the physical, chemical and microbiological composition of the activated sludge obtained even by the same purification process, as well as representing a danger from the sanitary and epidemiological point of view because of the possible presence in it of pathogenic microorganisms and helminths.

In practice the most widespread method of utilization of excess activated sludge produced at urban aeration stations as well as in the purification of effluents in a number of industries is anaerobic fermentation of activated sludge in a mixture with precipitates of effluents in sludge digesters. The methane thereby formed is used as a fuel and the fermented precipitate is partly dehydrated in air in sludge beds or in sludge ponds and is thereafter used as a fertilizer.

However, the above-mentioned method for dehydration and utilization of excess activated sludge requires considerable ground areas.

The dehydration of excess activated sludge by the methods known in chemical technology is either inefficient or requires great power consumption. This consumption is justified to a certain extent in the case that the dried activated sludge produced in biological purification of effluents, in a number of industries, is suitable for utilization as a fodder additive.

The known methods for dry distillation (pyrolysis) of activated sludge in a mixture with precipitates of wastewater involving the manufacture of useful products also require preliminary dehydration.

Therefore most of the methods and apparatus developed recently for rendering harmless excess activated sludge and wastewater precipitates relate to their dehydration and/or combustion. During dehydration various substances are added such as, for example, ash produced in combustion of sludge, coagulants, etc.

In addition, known in the art is "wet" oxidation of acidified activated sludge by heating it, as well as aerobic fermentation of activated sludge by treating it with oxygen.

A disadvantage of the known methods for processing activated sludge is the complexity and high cost of removal of vast amounts of water and such an inferior quality of products that it is hard to regard them as useful products. Besides, the combustion of activated sludge results in destruction of valuable substances it contained therein.

As pointed out above, activated sludge is a biomass of various microorganisms such as bacteria, protozoa, fungi, etc., and therefore it contains a number of valuable substances (proteins, carbohydrates, nucleic acids, lipids, vitamins, mineral substances) whose conservation and separation in the processing of activated sludge is an important problem.

An object of the present invention consists in developing a new technology for processing excess activated sludge ensuring the manufacture of useful products such as proteins, vitamin concentrates and fodder additives.

Said object has been attained in a method for processing excess activated sludge, which, according to the invention, comprises hydrolysis of said activated sludge at a pH of 0.01 to 6.0 and a temperature of 50° to 150° C. and/or its alkaline extraction at a pH of 9 to 13 and a temperature of 40° to 90° C.; formation of water-soluble protein, carbohydrate and mineral substances and vitamins taking place under the above-mentioned conditions of hydrolysis, and separation of protein substances under said conditions of alkaline extraction.

Three versions of realizing the proposed method for processing activated sludge are possible which we will further designate as a hydrolytic, an alkaline and a combined method.

The hydrolytic method for processing activated sludge, according to the invention, resides in carrying out the hydrolysis at a pH of 0.01 to 6.0 and a temperature of 80° to 150° C., the activated sludge being rendered harmless because of the death of pathogenic and toxicogenic organisms and the formation of water-soluble protein, carbohydrate and mineral substances and vitamins. The obtained suspension containing said substances may be directly used without any additional treatment as a culture medium for cultivating various microorganisms as well as for extracting from it individual products such as amino acids, oligopeptides, sugars and vitamins.

The alkaline version of processing activated sludge, according to the invention, comprises alkaline extraction of said activated sludge at a pH of 9 to 13 and a temperature of 40° to 90° C., the activated sludge being rendered harmless and water- and alkali-soluble protein substances being extracted from it, which are subsequently separated from the solution at the isoelectric point at a pH of 3.0 to 4.5.

The alkaline version of processing activated sludge makes it possible to obtain protein substances which may be used in feeding animals and poultry, as well as in those fields of industry which call for the use of protein additions.

The third version of processing activated sludge, which we have termed as combined, according to the invention, comprises simultaneous processing of a part of the activated sludge by hydrolysis and another part of the activated sludge by alkaline extraction.

According to the invention, this version of processing activated sludge comprises:
(a) hydrolysis of a part of the activated sludge at a pH of 0.5 to 6.0 and a temperature of 50° to 80° C.;
(b) separation of water-soluble protein, carbohydrate and mineral substances and vitamins formed during hydrolysis from the precipitate I containing mainly hard-to-dissolve polysaccharides and proteins;
(c) hydrolysis of the separated precipitate I at a pH of 0.01 to 0.5 and a temperature of 80 to 100° C., with additional formation of water-soluble protein, carbohydrate and mineral substances and vitamins taking place;

(d) separation of said water-soluble substances from the remaining precipitate II;

(e) washing said precipitate II with water;

(f) return of the washing water to the hydrolysis stage (a);

(g) simultaneous alkaline extraction of another part of the initial activated sludge at a pH of 9 to 13 and a temperature of 80° to 90° C.;

(h) separation of the solution of extracted protein substances from the resulting precipitate III of undissolved proteins and polysaccharides;

(i) precipitation of extracted protein substances from the solution at the isoelectric point at a pH of 3.0 to 4.5;

(j) separation of precipitated protein substances from the solution containing amino acids, vitamins, carbohydrates and mineral substances.

Thus, when realizing the proposed method according to the third version, it is possible to obtain protein substances, carbohydrates, vitamins and mineral substances. The solutions formed as a result of hydrolysis and alkaline extraction may be used as a culture medium for cultivating various microorganisms, since said solutions contain all the substances required for the growth and development of microorganisms.

The combined version of realizing the invention is preferable. The advantages of the invention will be understood from the following detailed description of said three versions of realizing the method.

Below is given a detailed description of processing activated sludge by hydrolysis.

The hydrolysis of activated sludge is carried out in the presence of an acid such as sulfuric, phosphoric or formic, at a pH of 0.01 to 6.0 and a temperature of 80° to 150° C. for 1 to 3 hours. In the process of hydrolysis the activated sludge is rendered harmless because of the death of pathogenic and toxicogenic organisms, and natural polymers are split. The hydrolysate formed contains proteins, sugars, amino acids, peptides, vitamins, mineral and other substances required for the growth and development of various microorganisms — yeasts (Candida, Hansenula etc.), mycelium fungi (Spicaria, Endomyces, Trichosporon, Penicillium, etc.), Actinomycetes (Streptomyces etc.) and bacteria (Bacillus, Bacterium, etc.).

The conditions of hydrolysis of the activated sludge are selected within said ranges of the pH, temperature, and time, depending on the requirements placed on the hydrolysate produced.

With a view of increasing the yield of monosugars, amino acids or reducing the consumption of the acid, the hydrolysis may be conducted under excess pressure, for example, up to 1 to 5 atm.

If required, individual compounds may be separated from said hydrolysate of the activated sludge, such as some amino acids, vitamins, peptides, and sugars.

The hydrolysate of the activated sludge may be delivered for fermentation, without adding any substances, as a culture medium for growing various microorganisms.

The growing of microorganisms on the hydrolysate of the activated sludge is conducted under these conditions which are necessary for the kind and strain of microorganisms being cultivated, both without additions and with addition of nutrient substances such as carbon sources.

As a result, a final product of fermentation is obtained, either in the form of a biomass, for example, when growing yeasts, or in the form of substances produced by the microorganisms being cultivated, for example, amino acids, antibiotics, etc.

The use of hydrolysates of the activated sludge in the microbiological industry makes it possible to save raw materials and subsidiary materials, such as sugars, amino acids, carbohydrates, nitrogen, phosphorus and potassium compounds. The consumption of such foodstuffs as meat and meat subproducts, and the consumption of such critical raw materials as corn steep liquor, and mineral fertilizers such as nitrogenous and phosphoric, and microelements, is reduced, and the conditions of growth and development of microorganisms are improved, and the yield of fermentation products such as biomass increases.

An advantage of the hydrolytic version is also that it is suitable for processing activated sludge produced in biological purification of various effluents and containing dry substances in a wide range of from 0.5 to 99.5%.

Below we propose a detailed description of the alkaline version of processing activated sludge.

To a suspension of activated sludge there is added an alkaline reactant such as sodium hydroxide, up to a pH of 9 to 13, heated at a temperature of 40° to 90° C. and kept at this temperature for 15 to 30 minutes, water- and alkali-soluble protein substances passing into the solution.

The treatment of activated sludge with an alkali at a temperature of 40° to 50° C. brings about the formation of a colloidal solution of a hygroscopic gel which contains all the useful substances of activated sludge including protein substances, and as such may be used in industry as a protein addition and its physical and chemical properties as those of a hygroscopic gel are also made use of.

Further heating of the gel at a temperature of 80° to 90° C. results in a possibility of separating the gel into a solution of protein substances and a precipitate mainly containing insoluble proteins and polysaccharides. The solution of protein substances is separated from the ballast precipitate, for instance by filtration or centrifugation, and an acid is added thereto to reach a pH of 3.0 to 4.5. A precipitate of protein substances which falls out from the solution in the isoelectric point at a pH of 3.0 to 4.5, is separated by any known method, for example, by filtration or centrifugation.

The protein substances produced from the alkaline extract of the activated sludge are a ready-made commercial product which is used, for example, for fodder.

Below we propose a description of the combined version of realizing the invention with a reference to a drawing which shows a flow sheet of the process.

From a vessel 1 a suspension of activated sludge is delivered to a device 2 where it is concentrated to a content of dry substances of 5 to 10%. The clarified water is delivered from the device 2 to a vessel 3.

The concentrated suspension of activated sludge is taken from the device 2 and delivered to a distribution device 4 wherein it is divided into two streams. One stream of the suspension of the activated sludge is fed into a device 5 where acidic hydrolysis is carried out, and the other stream is directed to a vessel 6 where alkaline extraction is conducted.

In the device 5 hydrolysis of the suspension of the activated sludge is conducted in soft conditions with an acid such as sulfuric, at a pH of 0.5 to 6.0 and a temperature of 50° to 80° C. for 10 to 60 minutes. A partial splitting of easy-to-hydrolyze natural polymers (proteins, polysaccharides, etc.) to form oligopeptides, amino acids and oligosaccharides which then pass into an aqueous solution, takes place. Besides, said conditions of hydrolysis bring about the rendering harmless of the activated sludge since they cause the death of pathogenic and toxicogenic microorganisms, helminths and other organisms. The hydrolysate of the activated sludge produced in the device 5 contains nutrient substances required for the growth and development of various microorganisms such as sugars, amino acids, oligopeptides, vitamins and mineral substances.

From the device 5 the hydrolysate produced is directed to a vessel 7 for subsequent neutralization to a pH within the range of 2.5 to 9.0. The pH value of the neutralized hydrolysate is set within said range depending on the microorganism which is to be cultivated on said hydrolysate. For example, in case of growing yeasts or mycellium fungi the optimal value of the pH is in the acid zone and in case of growing bacteria the optimal value of the pH is shifted to the alkaline zone.

From the vessel 7 the hydrolysate is directed to a dividing device 8 where the solution is separated from precipitate I, for example, by filtration or centrifugation.

From the dividing device 8 the aqueous solution containing peptides, amino acids, sugars, vitamins and mineral substances, is directed to a fermenter 9, wherein said solution is used as a culture medium for cultivating various microorganisms.

Precipitate I obtained in the dividing device 8 and mainly containing hard-to-hydrolyze polysaccharides, polypeptides, as well as mineral substances, is fed to a device 10 wherein it is subjected to hydrolysis under more severe conditions at a pH of 0.01 to 0.5 and a temperature of 80° to 100° C. for 30 to 60 minutes, a deeper splitting taking place of polysaccharides, proteins to form monosugars, amino acids, oligopeptides, and vitamins passing into an aqueous solution, and unhydrolyzed and hard-to-dissolve substances of the activated sludge which are wastes, remaining in precipitate II.

The hydrolysate obtained in the device 10 is directed to a dividing device 11 through which the solution of said substances is separated from said precipitate II.

Precipitate II obtained after separation in the device 11 is passed into the vessel 3, wherein the precipitate is washed with water coming from the device 2. The first washing water containing a large amount of acid is fed from the vessel 3 to the device 5 in lieu of acid and the second washing water is directed to the vessel 7.

The washed precipitate II from the vessel 3 may be delivered to the vessel 1 wherein it is used for acidification of the suspension of the activated sludge.

The second stream of the suspension of the activated sludge from the distribution device 4 is directed to the vessel 6 wherein alkaline extraction of said activated sludge is conducted at a pH of 9 to 13 and a temperature of 80° to 90° C. for 15 to 30 minutes, water-soluble and alkali-soluble protein substances as well as amino acids, vitamins and mineral substances passing into the solution. At the same time the activated sludge is being rendered harmless due to the death of pathogenic and toxicogenic organisms.

The alkaline extract is passed from the vessel 6 to a dividing device 12 wherein the solution of protein substances is separated from precipitate III mainly containing water- and alkali-insoluble proteins and polysaccharides.

Precipitate III obtained in the dividing device 12 is directed to the vessel 7 wherein it is used in lieu of alkali for neutralizing the acid hydrolysate. Due to this the alkali consumption is reduced and there is a saving in such important chemical substances as, for example, sodium hydroxide and ammonia.

The solution of protein substances from the dividing device 12 is directed to a vessel 13 for subsequent separation of protein substances. In the vessel 13 the pH of the protein extract is brought to 3.0 to 4.5 by adding thereto the hydrolysate produced in the dividing device 11. At a pH of 3.0 to 4.5 in the isoelectric point, precipitation of protein substances from the solution takes place. The suspension of protein substances is delivered from the vessel 13 to a dividing device 14 to separate the protein substances precipitated from the solution which is a commercial product suitable for use, for example, in feeding animals or in industries where protein additions are employed.

From the device 14 the aqueous solution mainly containing amino acids, vitamins and mineral substances, is directed to the fermenter 9 and used together with the hydrolysate obtained in the dividing device 8, as a culture medium for cultivating various microorganisms.

The cultivation of microorganisms is carried out under conditions optimal for a specific kind and strain of the microorganism taking into consideration its maximum productivity, both without addition and with addition of extra feeding sources. As a result of growing microorganisms on a culture medium prepared from the activated sludge a ready product of fermentation is obtained in the form of a biomass of microorganisms, for example yeasts, or in the form of a substance such as an antibiotic or an amino acid.

The proposed version is suitable for processing activated sludge produced in biological purification of different effluents and containing dry substances in a wide range — from 0.5 to 99.5%, therefore the activated sludge containing 0.5 to 2% of dry substances and conventionally produced in biological purification of effluents can be delivered for processing by the proposed method without preliminary treatment.

Thus, the proposed arrangement is a combination of treatment of the suspension of activated sludge by means of acid hydrolysis and alkaline extraction. The combined version of realizing the method is preferable since it makes it possible to process activated sludge in a closed circuit where the formation of effluents and wastes is reduced to a minimum. This is the main advantage of said circuit.

Besides, the proposed method for processing activated sludge has the following advantages, namely, it makes it possible:

to obtain a wide range of useful products such as protein substances, fodder additives, vitamin concentrates, culture mediums for cultivating various microorganisms, and solutions of physiologically active substances;

to exclude the processes of concentration and drying of activated sludge involving large power consumption;

to free large ground areas earlier intended for dehydrating activated sludge.

The method is not difficult to realize in industrial conditions since it is easily incorporated in the circuit of purification of effluents.

The invention makes it possible at the same time to obtain useful products and solve the problem of utilizing activated sludge formed in great excess in biological purification of effluents thereby ensuring intensification of purification of effluent, improvement of the quality of the purified water and decrease in the pollution of the environment.

For a better understanding of the present invention specific examples are given below for illustration wherein Example 1 is given with a reference to the drawing.

EXAMPLE 1

A suspension concentrated in the device 2 of activated sludge produced in biological purification of domestic effluents and containing 5 percent by weight of dry substances, in an amount of 40 l is transferred to the distribution device 4 wherein the suspension is divided in two parts.

One part of the suspension in an amount of 20 l is directed to the device 5 wherein hydrolysis with acid is carried out, and the other part in an amount of 20 l is directed to the vessel 6 wherein alkaline extraction is conducted.

In the device 5 there is added to the suspension of activated sludge 25 g of concentrated sulfuric acid and hydrolysis is carried out at a pH of 0.9 to 1.1, a temperature of 50° C. for 40 minutes while agitating.

The hydrolysate produced is transferred from the device 5 to the vessel 7 for subsequent neutralization.

Alkaline extraction of the other part of the suspension of activated sludge is carried out in the vessel 6. To this end to 20 l thereof there is added while agitating 2.5 ml of a 40% sodium hydroxide aqueous solution to a pH of 10.5. The extract produced is heated to 85° C. and maintained for 30 minutes.

From the vessel 6 the alkaline extract is directed to the dividing device 12 through which the solution of protein substances is separated and fed to the vessel 13.

The precipitate obtained in the device 12 and mainly containing proteins and polysaccharides undissolved in the aqueous and alkaline solution is fed to the vessel 7 wherein it is used for neutralization of hydrolysis products obtained in the device 5.

The hydrolysate of activated sludge neutralized to a pH of 4.2 is transferred from the vessel 7 to the device 8 through which the precipitate is separated from the solution containing oligopeptides, amino acids, sugars, vitamins and mineral substances. Said solution is delivered to the fermenter 9.

The precipitate separated in the device 8 and mainly containing hard-to-hydrolyze polysaccharides, proteins and mineral substances, is transferred to the device 10 wherein said precipitate is subjected to hydrolysis under more severe conditions at a pH of 0.01 and a temperature of 90° C. for 40 minutes.

From the device 10 the hydrolysate is transferred to the device 11 wherein it is separated into a precipitate and a solution. Said precipitate containing unhydrolyzed substances of activated sludge such as cellulose and hard-to-dissolve mineral substances is transferred to the vessel 3 wherein it is twice washed with water. The first washing water is delivered to the device 5 and the second to the vessel 7 and the washed precipitate is removed.

The acid solution of hydrolysis products obtained in the device 11 is sent to the vessel 13 wherein it is used instead of acid for acidification of the alkaline solution of protein substances to a pH of 3.2 at which proteins fall out from the solution into a precipitate. The fallen-out precipitate of protein substances is separated from the solution in the device 14, which results in obtaining a ready product in an amount of 62 g containing 54% of proteins, 16%, of carbohydrates and 25% of mineral substances which can be used, for example for fodder.

The solution separated from the precipitate of protein substances in the device 14 and containing amino acids, sugars, peptides, vitamins and mineral substances, is directed to the fermenter 9.

In the fermenter 9 there is carried out continuous cultivation of yeasts *Candida acottii* at a pH of 4.0 to 4.2, a temperature of 35° C. ± 1° C., and the medium flow rate $D = = 0.1$ hour$^{-1}$.

The solutions coming from the devices 8 and 14 are used as a culture medium.

The biomass of yeast is produced with a weight of 33.5 g/l as for absolute dry substance. The yield of the product is 63% of the absolute dry substance of the initial activated sludge. The dried yeast contains 52% of raw protein, all the important amino acids and vitamins of Group B, and can be used as a fodder.

EXAMPLE 2

The processing of activated sludge is carried out as described in Example 1, except that the hydrolysis of the activated sludge suspension is carried out in the device 5 at a pH of 0.5 and a temperature of 80° C. for 10 minutes, and in the device 10 at a pH of 0.02 and a temperature of 100° C. for 1 hour. The same yield of the biomass of yeast is obtained.

EXAMPLE 3

To 1 liter of the activated sludge suspension obtained in biological purification of effluents from the fodder yeast production and containing 2.5% of absolute dry substance there is added one ml of a 1% sulfuric acid solution, heated to 100° C. and maintained at 100° C. and a pH of 5.5 to 6.0 for 1 hour. The solution produced containing mainly amino acids, vitamins and mineral substances is filtered from the precipitate and poured into flasks. After sterilization of said flasks they are inoculated with yeast *Candida tropicalis* which is then cultivated in a shaker at a temperature of 33° C. In 48 hours of growth the biomass of yeast is produced with a weight of 2.5 g/l; the yield is 10% of the absolute dry substance of the initial activated sludge.

EXAMPLE 4

To 1 liter of the activated sludge suspension obtained in biological purification of effluents from the fodder yeast production and containing 2.5% of dry substance there is added 27 ml of the concentrated sulfuric acid. The mixture is heated in a boiling water bath to 80° C. and the hydrolysis is conducted at a pH of 0.01 for 1 hour while agitating periodically. The hydrolysate solution is separated from the precipitate by decantation. To the solution produced containing amino acids, sugars, vitamins and mineral substances, there is added potassium hydroxide to a pH of 5.5 after which it is used as a culture medium for growing yeast. Said culture medium is poured into flasks, sterilized and inoculated with a culture of the yeast Candida Sp. The growing of the yeast is conducted in a shaker at a temperature of 35° C. In 48 hours of growth the biomass of the yeast is produced with a weight of 24.3 g/l. The yield of the product is 93.2% of the absolute dry substance of the initial activated sludge.

EXAMPLE 5

To 20 l of the activated sludge suspension from the effluents purification station with a concentration of dry substances of 5% there is added a 40% potassium hydroxide aqueous solution to a pH of 9.2 and heated to 40° C. A hygroscopic gel is formed which can be used in industry as a protein additive or as a hygroscopic gel.

EXAMPLE 6

The treatment of the activated sludge suspension is conducted in the same manner as in Example 5 except that the heating is carried out at a temperature of 80° C. for 15 minutes. The produced solution of protein substances is separated by filtration from the precipitate, the precipitate is discarded and the solution of protein substances is acidified with sulfuric acid to a pH of 3.8. The proteins fall out into precipitate. The solution separated by centrifugation can be used as an addition for a culture medium in growing microorganisms. The obtained precipitate of protein substances containing 56% of protein, 15% of carbohydrates and 24% of ash can be used, for example, as a protein additive in feeding animals and fowl. The yield of protein substances is 6% of the absolute dry substance of the initial activated sludge.

What we claim is:

1. A method for processing activated sludge into useful products, which comprises subjecting a first portion of said activated sludge to hydrolysis at a pH of 0.01 to 6.0 and a temperature of 50° to 150° C., thus forming a solution of water soluble proteins, carbohydrates, mineral substances and vitamins, and a first precipitate which is acid, separating said solution of water-soluble proteins, carbohydrates, mineral substances and vitamins from said first precipitate, subjecting a second portion of said activated sludge to alkaline extraction at a pH of 9 to 13 and a temperature of 40° to 90° C., thus forming a solution of soluble proteins and another precipitate which is alkaline and separating said solution of soluble proteins from said other precipitate.

2. The method of claim 1, wherein the hydrolysis of the activated sludge is conducted at a pH of 0.01 to 6.0 and a temperature of 80° to 150° C..

3. The method of claim 1, wherein the alkali extraction is conducted at a pH of 9 to 13 and a temperature of 80° to 90° C. with subsequent precipitation of protein substances from the solution in the isoelectric point at a pH of 3.0 to 4.5.

4. The method of claim 1,
   wherein the hydrolysis of said first portion of said activated sludge is effected at a pH of 0.5 to 6.0 and a temperature of 50° to 80° C.
   the separated first precipitate is subjected to further hydrolysis at a pH of 0.01 to 0.5 and a temperature of 80° to 100° C., thus forming an additional solution or waterOsoluble proteins, carbohydates, mineral substances and vitamins
   and a second precipitate which is acid, separating said additional solution of water-soluble substances from said second precipitate
   washing said second precipitate with water
   returning the washing water to the first hydrolysis state,
   subjecting said second portion of said activated sludge to alkaline extraction at a pH of 9 to 13 and a temperature of 80° to 90° C.
   thus forming a further solution of soluble proteins and a third precipitate which is alkaline and which includes undissolved proteins and polysaccharides,
   precipitating the extracted protein substances from said further solution at the isoelectric point at a pH of 3.0 to 4.5,
   said separating the precipitated protein substances from the remaining solution which contains amino acids, vitamins, carbohydrates and mineral substances.

5. The method of claim 4, wherein said solutions containing water-soluble protein, carbohydrate, mineral substances and vitamins are used in a culture medium for the fermentation of microorganisms.

6. The method of claim 1 and wherein said first precipitate is washed with water to obtain an acidic wash water which is utilized for acidification of additional activated sludge.

7. The method of claim 1 and wherein said other precipitate which is alkaline is utilized for the neutralization of the acid hydrolysate obtained from said first portion of said activated sludge.

8. The method of claim 6 and wherein said other precipitate which is alkaline is utilized for the neutralization of the acid hydrolysate obtained from said first portion of said activated sludge.

* * * * *